United States Patent [19]

McCoy

[11] Patent Number: 5,167,655
[45] Date of Patent: Dec. 1, 1992

[54] COLD THERAPY PANTY

[76] Inventor: Kevin McCoy, 3612 Double Rock La., Baltimore, Md. 21234

[21] Appl. No.: 692,919

[22] Filed: Apr. 29, 1991

[51] Int. Cl.$^5$ .............. A61F 13/15; A61F 13/20; A41B 9/04
[52] U.S. Cl. .................. 604/396; 604/385.1; 604/395; 2/406; 2/408
[58] Field of Search .......... 128/401, 402, 403; 604/385.1, 395, 396, 398, 400, 401, 402; 2/408

[56] References Cited

U.S. PATENT DOCUMENTS

| 2,748,772 | 6/1956 | Titone et al. | |
|---|---|---|---|
| 3,175,558 | 3/1965 | Caillouette et al. | 128/403 |
| 3,608,551 | 9/1971 | Seijo | 604/396 |
| 3,809,096 | 5/1974 | York | 128/403 |
| 3,871,376 | 3/1975 | Kozak | 128/403 X |
| 3,885,403 | 5/1975 | Spencer | 128/403 X |
| 3,950,158 | 4/1976 | Gossett | 128/403 X |
| 4,055,188 | 10/1979 | Pelton | |
| 4,145,763 | 3/1980 | Abrams et al. | |
| 4,352,356 | 10/1982 | Tong | 604/398 X |
| 4,397,315 | 8/1983 | Patel | 128/403 |
| 4,695,279 | 9/1987 | Steer | 604/401 X |
| 4,938,221 | 7/1990 | Tuffel | 128/403 X |
| 4,940,463 | 7/1990 | Leathers et al. | 604/396 |

Primary Examiner—David Isabella
Assistant Examiner—Elizabeth M. Burke
Attorney, Agent, or Firm—Banner, Birch, McKie & Beckett

[57] ABSTRACT

A cold therapy panty is provided which includes a front portion and a back portion with a crotch area formed therebetween. A receptacle is located adjacent the crotch area of the panty and extends along the crotch area. An absorbent pad for absorbing bodily fluids and a cold pack for applying cold therapy to the crotch of the wearer are inserted into the receptacle. Alternatively, the absorbent pad may be attached to the inner side of the panty to avoid soiling the pouch and panty. Mating fasteners on the front and back portions are connected to attach the panty to the wearer.

6 Claims, 3 Drawing Sheets

COLD THERAPY PANTY

BACKGROUND OF THE INVENTION

The present invention generally relates to a combination panty with absorbent pad and cold therapy pack for the application of cold therapy to the crotch area of the wearer. For example the cold therapy panty of the present invention may be used to reduce pain and swelling associated with the surgical enlargement of the vulval, and other surgical procedures related to the vaginal or anal area.

Prior art panties have combined a panty with a sanitary napkin or pad. In U.S. Pat. No. 2,748,772 to Titone, a combination lady's panty and sanitary napkin is disclosed which is disposable and prevents the passage of menstrual discharge. However, Titone's panty does not attempt to provide any medical therapy to the crotch area, such as the application of cold therapy.

The application of cold can offer an analgesic effect in the relief of pain and discomfort associated with surgical enlargement of the vulval, and other surgical procedures. Cold therapy also enhances the healing process in these areas and also reduces swelling and edema. The added benefit of cold thickening blood also helps to clot excessive bleeding. Prior art panties have not addressed this need for a panty which allows the application of cold therapy to the vaginal or anal areas.

Accordingly, a need has arisen for a panty having an absorbent pad and a cold therapy pack to provide cold therapy to the vaginal or anal areas.

SUMMARY OF THE INVENTION

Therefore, it is an object of the present invention to provide a panty having an absorbent pad and a cold therapy pack to treat many of the problems associated with post child-birth, vaginal or anal operations, and many diseases or medical problems occurring in the crotch area.

It is a further object of the present invention to provide a cold therapy panty which is disposable.

It is a further object of the present invention to provide a cold therapy panty which has a receptacle for the use of a reusable cold pack.

It is yet another object of the present invention to provide a cold therapy panty which has an absorbent pad for the absorption of vaginal discharge, blood or other bodily fluids.

It is yet another object of the present invention to provide a panty which is easily attached to the wearer.

In accordance with the present invention, a cold therapy panty is provided for the application of cold therapy having front and back portions, with a crotch area formed therebetween, and inner and outer sides. The cold therapy panty includes a receptacle or pouch attached to or formed within the inner side of the panty which extends along the crotch area, an absorbent pad attached to or inserted within the receptacle for the absorption of bodily fluids, and a cold pack inserted into the receptacle for the application of cold therapy to the wearer's crotch.

BRIEF DESCRIPTION OF THE DRAWINGS

A more complete appreciation of the present invention and many of the attendant advantages thereof will be readily obtained as the invention becomes better understood by reference to the following detailed description when considered in connection with the accompanying drawings.

DETAILED DESCRIPTION

Figure 1:
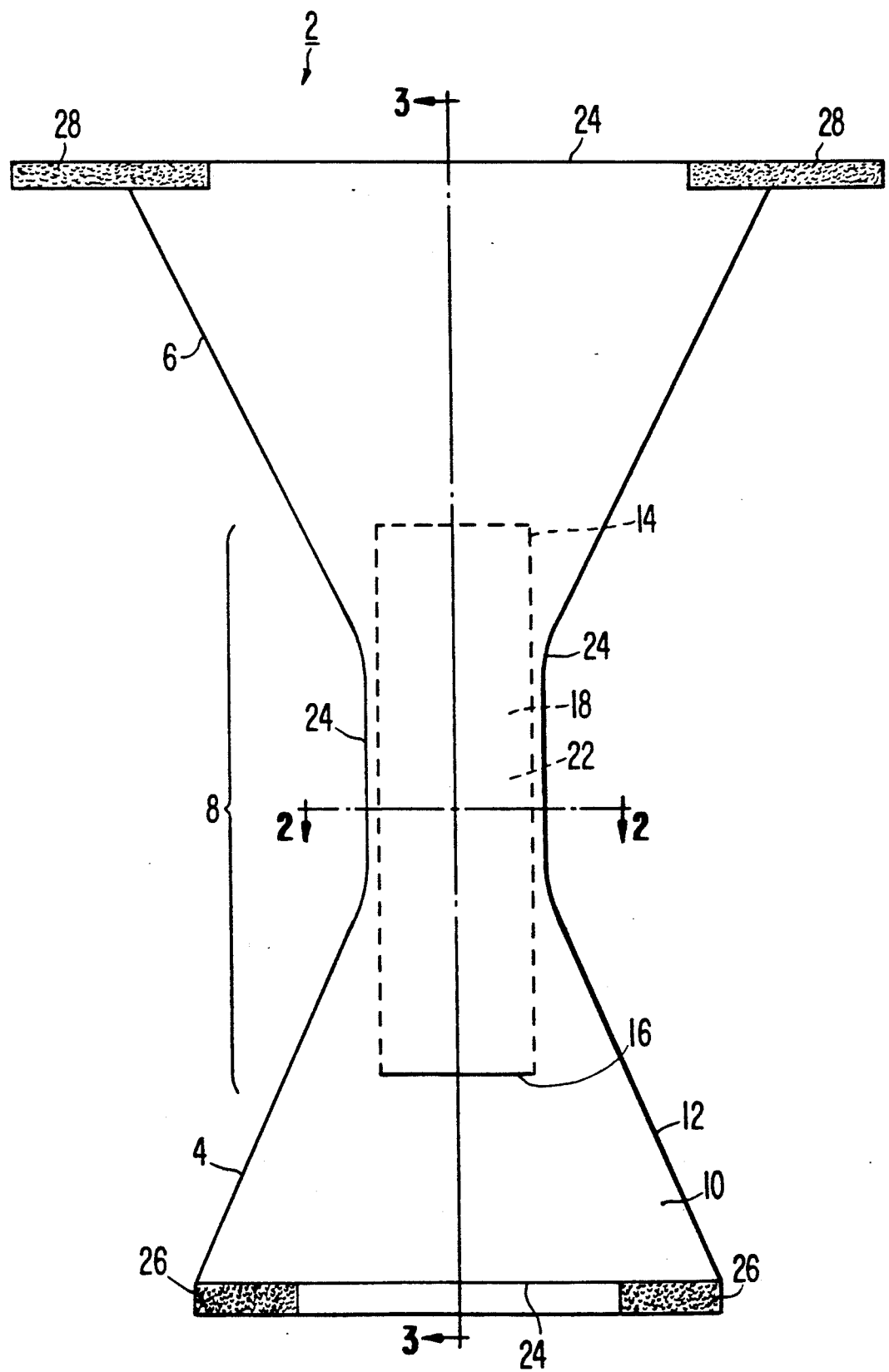
FIG. 1 is a diagram of a cold therapy panty in accordance with a first preferred embodiment of the present invention.

Referring to the drawings in detail, wherein like numerals indicate like elements, FIG. 1 is a diagram of a cold therapy panty in accordance with a first preferred embodiment of the present invention. Cold therapy panty 2 has an inner side 10, outer side 12, front portion 4 and back portion 6. When cold therapy panty 2 is properly attached to a wearer, front portion 4 covers the front surface of the wearer, while back portion covers the rear surface of the wearer. Inner side 10 is adjacent the wearer while outer side 12 forms the external or outer side of cold therapy panty 2. Crotch area 8 is formed between front portion 4 and back portion 6 and generally covers the crotch of the wearer, including the vaginal and/or anal areas.

Figure 2:
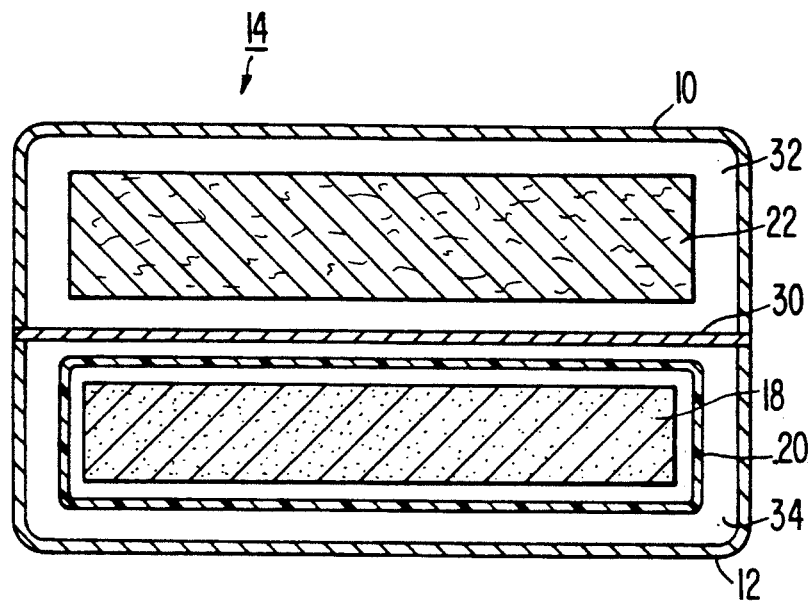
FIG. 2 is a sectional view taken generally along the lines 2—2 of FIG. 1.
Figure 3:
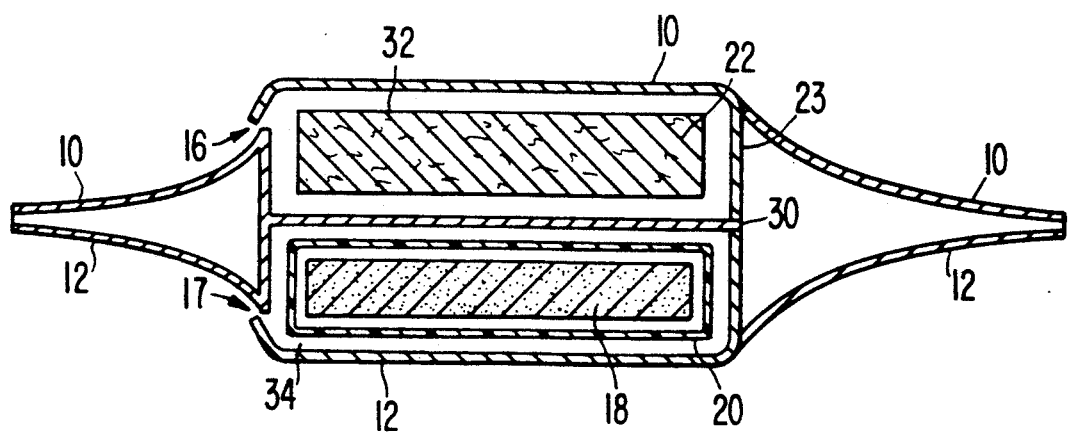
FIG. 3 is a sectional view taken generally along the lines 3—3 of FIG. 1.

Receptacle 14 may comprise one or more pouches or other receiving means and is located generally on or adjacent to crotch area 8. As best seen in FIGS. 2-3, receptacle 14 is preferably formed between inner side 10 and outer side 12 and extends substantially along crotch area 8 of cold therapy panty 2. Alternatively, receptacle 14 may be sewn or otherwise attached to either inner side 10 or outer side 12 of panty 2. Receptacle 14 encloses absorbent pad 22 and cold pack 18. Absorbent pad 22 is located adjacent inner side 10 to absorb blood, vaginal discharge or other bodily fluids from the wearer. Cold pack 18 is located adjacent outer side 12 to prevent soiling from bodily fluids and applies cold therapy generally to the crotch of the wearer. Cold pack 18 is preferably enclosed in plastic bag 20 to provide additional protection against soiling of cold pack 18 and allow cold pack 18 to be reusable.

Receptable 14 comprises pouches 32 and 34. Separating layer 30 is optional and divides receptacle 14 into separate pouches 32 and 34 and slightly insulates cold pack 18 from the wearer in order to prevent hypothermia. Inner side 10 is preferably constructed of a material which is permeable to bodily fluids to allow absorbed pad 22 to function properly. It is also desirable that inner side 10 and layer 30 are sufficiently permeable to a temperature differential to allow the application of cold therapy to the wearer.

As seen in FIG. 3, receptacle 14 has pouch opening 16 positioned adjacent inner side 10 and front portion 4 to allow for the insertion and removal of absorbent pad 22 or other medical aids into pouch 32. Receptacle 14 also has pouch opening 17 located adjacent outer side 12 and front portion 4 for the insertion and removal of cold pack 18 or other medical aids into pouch 34. Each pouch within receptacle 14 may receive an absorbent pad, cold pack or other medical aid.

Alternatively, receptacle 14 may comprise only a single pouch for the insertion of cold pack 18 and absorbent pad 22. In this case, separating layer 30 may be attached only at one end or deleted altogether. In addition to having a pouch opening located on front portion 4, receptacle 14 may also have a pouch opening or openings located on back portion 6 such that a pad or cold pack may be inserted or removed through either the front 4 or back 6 portions. Pouch openings 16 and 17 are preferably sealable or closable through the use of tape, snaps, hook and pile fasteners or the like. However, because pad 22 and pack 18 are located below pouch openings 16 and 17 when panty 2 is attached to the wearer, gravity may provide sufficient retention to prevent the escape of pad 22 or pack 18 without the use of additional sealing means.

Alternatively, absorbent pad 22 may be attached to inner side 10 using tape or other fastener, and not inserted into receptacle 14 to prevent the soiling of cold therapy panty 2, including receptacle 14. Absorbent pad 22 may contain super-absorbent polymer materials to enhance absorption. In addition, receptacle 14 may be used to receive a hot pack for the application of hot therapy to the wearer. Cold pack 18 may be any type of conventional pre-cooled gel or the like and is preferably soft and flexible when cooled to provide the wearer maximum comfort. For example, a hydrophilic gel similar to the gel described in U.S. Pat. No. 4,243,041 to Paul may be used for this purpose.

Cold therapy panty 2 preferably includes elastic members 24 attached to the waist of panty 2 and edges of crotch area 8. Elastic members 24 may include elastic bands or any other flexible or stretchable material and are provided for keeping receptacle 14 firmly in the crotch of the wearer to promote the absorption of bodily fluids by absorbent pad 22 and prevent the escape of fluids or discharge down the wearer's leg. Cold therapy panty 2 also includes fasteners 26 and 28 located on the edges of front side 4 and rear side 6 respectively. Fasteners 26 and 28 may be of any conventional type such as tape, snaps, belt and loop, etc., but are preferably hook and pile type fasteners. Fasteners 26 are connected to fasteners 28 to connect front portion 4 to rear portion 6 in order to attach cold therapy panty 2 to the wearer.

Cold therapy panty 2 may be used for a variety of purposes, including but not limited to the application of cold therapy to the vaginal area during post birth in order to reduce pain, swelling and edema. The application of cold offers an analgesic effect in the relief of pain and discomfort associated with the surgical enlargement of the vulval, and other surgical procedures related to the vaginal area. The application of cold may also aid in the healing process and the benefit of cold thickening blood may help to clot excessive bleeding. Cold therapy panty 2 also assists in the capturing and absorption of post birth bleeding, discharge or other bodily fluids. Cold therapy panty 2 may also be used to reduce problems associated with other vaginal operations, anal operations, hemorrhoids, herpes, venereal disease, etc., or any surgical procedure or medical complication related to the crotch where cold therapy may be beneficial. Cold therapy panty 2 may also be used for the application of hot therapy to the crotch of the wearer.

Cold therapy panty 2 may be constructed from any suitable material, but is preferably disposable and made from an absorbent paper product or the like. Absorbent pad 22 is preferably inserted into receptacle 14 along with cold pack 18. Absorbent pad 22 may also be attached to inner side 10 using adhesive or other fastener. If cold therapy panty 2 is designed as disposable, it is also contemplated that cold therapy panty may have a built in feminine napkin/pad such that cold therapy panty 2 and absorbent pad 22 are constructed as a single integral unit. Cold pack 18 is preferably enclosed in plastic bag 20 prior to being inserted into receptacle 14 to prevent the soiling and allow the reuse of cold pack 18.

Alternatively, cold therapy panty 2 may be constructed of a washable material to allow panty 2 to be reused. When cold therapy panty 2 is designed to be reusable, absorbent pad 22 may be inserted into pouch 14 along with cold pack 18. However, where cold therapy panty 2 is designed to be reusable, absorbent pad 22 is preferably attached to inner side 10 to prevent the soiling of cold therapy panty 2.

Figure 4A:
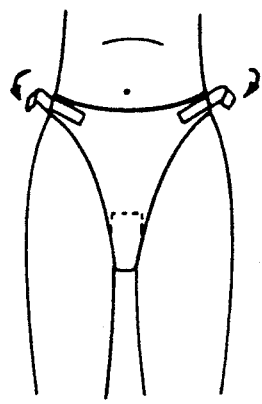
FIG. 4A is a front view of the cold therapy panty of FIG. 1.
Figure 4B:
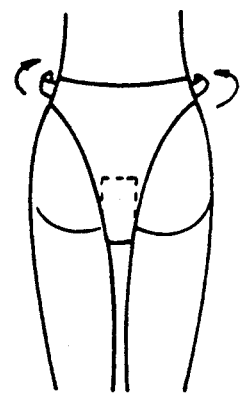
FIG. 4B is a back view of the cold therapy panty of FIG. 1.
Figure 4C:
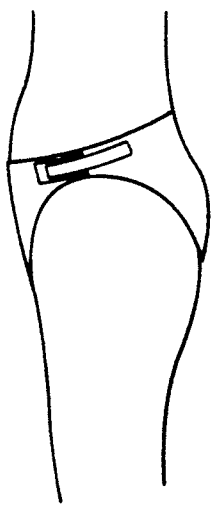
FIG. 4C is a side view of the cold therapy panty of FIG. 1.

FIGS. 4A-4C are front, back and side views respectively of the cold therapy panty 2 of FIG. 1. Referring to FIGS. 1 and 4A-4C, the arrows of FIGS. 4A and 4B illustrate how fasteners 26 and 28 are connected in order to attach cold therapy panty to the wearer. Fasteners 26 and 28 are preferably velcro hooks but any conventional fastener may be used. Fasteners 26 are connected to and mate with fasteners 28 on both the left and right sides of cold therapy panty 2 over the hips of the wearer to provide a comfortable and snug fit.

Figure 5:
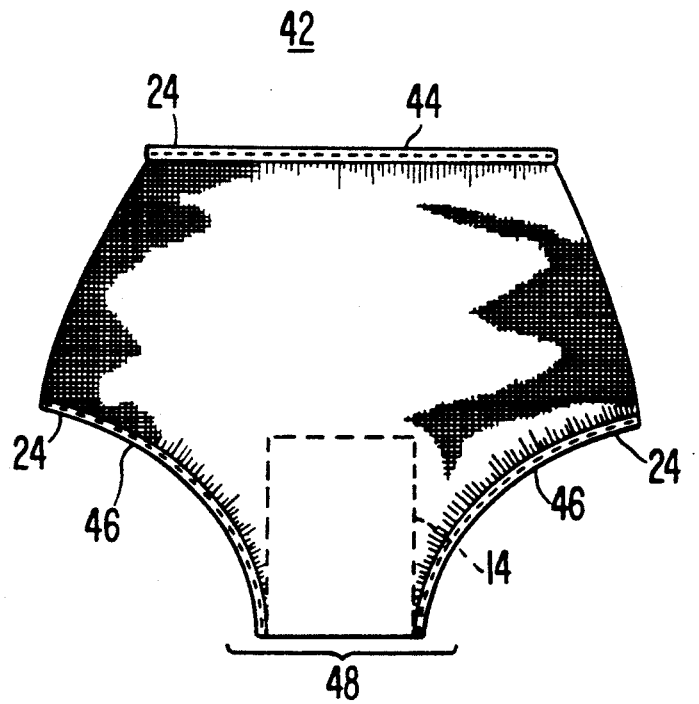
FIG. 5 is a diagram of a cold therapy panty in accordance with a second preferred embodiment of the present invention.

FIG. 5 is a diagram of a cold therapy panty according to a second preferred embodiment of the present invention. Slip-on cold therapy panty 42 is preferably disposable and contains waist opening 44 and leg openings 46. Elastic members 24 extend substantially around the edges of waist opening 44 and leg openings 46 to provide the wearer a more comfortable fit. Crotch area 48 is formed between leg openings 46 and covers the crotch of the wearer. As in the first preferred embodiment, receptacle 14 is located adjacent crotch area 48 and extends substantially along crotch area 48 and may be formed within or attached to the inner side of panty 42. Absorbent pad 22 may be inserted into receptacle 14 and absorbs discharge or other bodily fluids. Cold pack 18 is inserted into receptacle 14 and is located adjacent to and outward from absorbent pad 22 to avoid coming into contact with bodily fluids. Cold pack 18 is preferably reusable may also be enclosed in a plastic bag for additional protection from being soiled. It is contemplated that a disposable slip-on panty may have the absorbent pad 22 built into panty 42 such that pad 22 and panty 42 are constructed as a single integral unit. If panty 42 is constructed as a washable and reusable unit, absorbent pad 22 preferably is attached to the inner side of panty 42, and not inserted into pouch 14 to avoid excess soiling of receptacle 14 and panty 42.

This invention has been described in detail in connection with the preferred embodiments but is for illustrative purposes only and the invention is not limited thereto. It will be easily understood by those skilled in the art that variations and modifications can be easily made within the scope of this invention as defined by the appended claims.

I claim:

1. A panty comprising front and back protions, with a crotch area formed therebetween, an inner side of said panty being closest to a wearer, an outer side of said panty disposed outwardly from said inner side, a separating layer disposed between said inner side and said outer side forming a first and a second receptacle, an absorbent pad, and a cold pack for the application of cold therapy, said first receptacle extending along the crotch area and formed between said inner side and said separating layer to receive said absorbent pad, and said second receptacle extending along the crotch area and formed between said separating layer and said outer side to receive said cold pack.

2. The panty according to claim 1 wherein said panty is disposable.

3. The panty according to claim 1 wherein said panty is washable and reusable.

4. The panty according to claim 1 wherein said cold pack is enclosed in plastic.

5. The panty according to claim 1, further comprising fastening means located substantially on edges of the front and back portions of said panty to allow the connection of the front and back portions to attach the panty to the wearer.

6. The panty according to claim 1, further comprising elastic members located along outer edges of the crotch area and along a waist area of the panty.

* * * * *